US012311758B2

(12) United States Patent
Van Valer (10) Patent No.: US 12,311,758 B2
(45) Date of Patent: May 27, 2025

(54) IMPAIRED DRIVER DETERRENT SYSTEM

(71) Applicant: Andrew Lee Van Valer, Reno, NV (US)

(72) Inventor: Andrew Lee Van Valer, Reno, NV (US)

(73) Assignee: Invisible Holdings, LLC, Sheridan, WY (US)

( * ) Notice: Subject to any disclaimer, the term of this patent is extended or adjusted under 35 U.S.C. 154(b) by 0 days.

(21) Appl. No.: 18/625,719

(22) Filed: Apr. 3, 2024

(65) Prior Publication Data

US 2024/0326590 A1 Oct. 3, 2024

Related U.S. Application Data

(60) Provisional application No. 63/493,866, filed on Apr. 3, 2023.

(51) Int. Cl.
*B60K 28/06* (2006.01)
*A61B 5/18* (2006.01)
(Continued)

(52) U.S. Cl.
CPC ............... *B60K 28/02* (2013.01); *A61B 5/18* (2013.01); *B60K 28/063* (2013.01);
(Continued)

(58) Field of Classification Search
CPC ...... B60K 28/02; B60K 28/06; B60K 28/063; B60K 2028/006; B60K 2028/003;
(Continued)

(56) References Cited

U.S. PATENT DOCUMENTS 4,645,939 A * 2/1987 Robinson ............. B60K 28/063
340/576
4,809,810 A * 3/1989 Elfman ............... G01N 33/4972
340/576
(Continued)

FOREIGN PATENT DOCUMENTS

KR 101075511 B1 * 10/2011
KR 102249312 B1 * 5/2021
(Continued)

*Primary Examiner* — Keith J Frisby
(74) *Attorney, Agent, or Firm* — Donald R. Boys; Central Coast Patent Agengy LLC (57) ABSTRACT

A system preventing an impaired driver from starting a vehicle has a mobile application executing on a portable communication device having a display screen, user-operable input elements, a microphone audio input, a speaker and wireless communication circuitry, a hardware component integrated into wiring of the vehicle, the hardware component comprising a normally open switching element operable by wireless signal from the portable communication device, that when open prevents the vehicle from starting, and an interactive interface displayed on the display screen.

The interactive interface requests specific action from a candidate driver, records the candidate driver's action, determines if the action indicates the candidate driver is impaired, and if not impaired, signals the hardware component wirelessly to close the normally open switching element for a predetermined time, enabling the candidate driver to start the vehicle.

7 Claims, 6 Drawing Sheets

(51) Int. Cl.
*B60K 28/02* (2006.01)
*B60R 16/033* (2006.01)
*B60K 28/00* (2006.01)
*B60W 40/08* (2012.01)
*H04W 4/48* (2018.01)

(52) U.S. Cl.
CPC ...... *B60R 16/033* (2013.01); *B60K 2028/003* (2013.01); *B60W 2040/0818* (2013.01); *B60W 2040/0836* (2013.01); *B60W 2040/0845* (2013.01); *B60W 2040/0863* (2013.01); *B60W 2040/089* (2013.01); *B60W 2540/24* (2013.01); *B60W 2540/26* (2013.01); *H04W 4/48* (2018.02)

(58) Field of Classification Search
CPC ........ B60R 16/03; B60R 16/033; H04W 4/48; B60W 2040/0818; B60W 2040/0827; B60W 2040/0836; B60W 2040/0845; B60W 2040/0854; B60W 2040/0863; B60W 2040/089; B60W 2540/024; B60W 2540/026; A61B 5/18
USPC .......................... 180/272; 340/576; 307/10.6
See application file for complete search history.

(56) References Cited

U.S. PATENT DOCUMENTS

2005/0212668 A1* 9/2005 Allison, III ............ B60R 22/48
 340/457.1
2018/0306776 A1* 10/2018 Cado .................. G01N 33/4972
2024/0336227 A1* 10/2024 Tucker ................ B60R 25/2063

FOREIGN PATENT DOCUMENTS

RU 2006105914 A * 10/2007
WO WO-9301072 A1 * 1/1993 ........... B60R 25/045

* cited by examiner

IMPAIRED DRIVER DETERRENT SYSTEM

CROSS-REFERENCE TO RELATED APPLICATIONS

The instant application claims priority to a Provisional Patent Application (PPA) 63/493,866 filed Apr. 3, 2023. The full disclosure of the parent application is incorporated at least by reference.

BACKGROUND OF THE INVENTION

1. Field of the Invention

The present invention is in the technical field of controls for vehicles and pertains more particularly to a system that tests candidate drivers for impairment.

2. Description of Related Art

It is well-known in the art that there are a lot of drivers on the road that should not be driving. Driving under the influence (DUI) is a big problem everywhere, and death, injuries and property damage is a direct result. DUI typically refers to alcohol abuse, but there are many other substances that, if ingested or used irresponsibly may impair a person's ability to safely operate a vehicle.

One proposed solution to DUI is an ignition interlock device (IID). An IID is a handheld car breathalyzer device that measures the amount of alcohol in your breath. Installing one in a driver's automobile is a common requirement following a drunk driving conviction. In simplest terms, an IID is an in-car breathalyzer that prevents a person from starting a car until a breath alcohol test is taken. An ignition interlock device is a proper term for devices sometimes referred to as "in-car breathalyzer" or "car interlock" or "blow and go".

There are a number of such devices commercially available, and there are a variety of technology solutions as to how the devices integrate with a vehicle to prevent a driver who is inebriated from starting the vehicle. A common circumstance with such devices is that they are complicated and expensive to install, and typically require a trained technician to install and test. Another problem is that IIDs typically do not detect impairment beyond alcohol level in a candidate driver's breath.

What is clearly needed is a system that detects impairment in a very general sense and is also straightforward and inexpensive to install and use.

BRIEF SUMMARY OF THE INVENTION

In an embodiment of the invention a system preventing an impaired driver from starting a vehicle is provided, comprising a mobile application executing on a portable communication device having a display screen, user-operable input elements, a microphone audio input, a speaker and wireless communication circuitry, a hardware component integrated into wiring of the vehicle, the hardware component comprising a normally open switching element operable by wireless signal from the portable communication device, that when open prevents the vehicle from starting, and an interactive interface displayed on the display screen. The interactive interface requests specific action from a candidate driver, records the candidate driver's action, determines if the action indicates the candidate driver is impaired, and if not impaired, signals the hardware component wirelessly to close the normally open switching element for a predetermined time, enabling the candidate driver to start the vehicle.

In one embodiment, after the predetermined time, the switching element is allowed to return to open status. Also, in one embodiment the display screen is a touchscreen, and the specific action requested is a touch screen action indicated by one or more of display elements and text. Also, in an embodiment the display screen displays an arrow, and the candidate driver is instructed by either text or audio from the speaker to swipe the screen in the direction of the arrow displayed. And in one embodiment the candidate driver's reaction time is measured and compared to stored reaction times in determining whether the candidate driver is impaired.

In one embodiment the display screen displays a text entity, and the candidate driver is requested either by text or by audio from the speaker to read the text entity aloud. Also, in an embodiment the candidate driver's reading of the text entity aloud is recorded through the microphone, and compared to stored recordings by impaired and by unimpaired persons in a process of determining if the candidate driver is impaired.

In one embodiment of the system the hardware component comprises an enclosure with an input terminal, and output terminal, a normally open switching element in a line between the input and the output terminal, a processor executing coded instructions from a data repository, wireless communication circuitry coupled to the processor and a battery powering electronic components. Also, in one embodiment the hardware component comprises a cylindrical fuse having a first portion with a first conductor leading from a contact end to a switching element operated by a processor executing coded instructions from a coupled data repository, in response to a signal received via wireless communication circuitry coupled to the processor, a second conductor leading from the switching element to a first end of a fuse filament in a second portion, and a third conductor leading from a second end of the fuse filament to a second contact end. In one embodiment the first and second portions of the cylindrical fuse are separable, such that in event of a blown fuse filament, only the second portion with the fuse filament has to be replaced.

In one embodiment of the system the hardware component comprises a smart fuse with a body having a first and a second spade connector adapted to plug into an automobile fuse and relay center, a first conductor leading from the first spade connector to a switching element operated by a processor executing coded instructions from a coupled data repository, in response to a signal received via wireless communication circuitry coupled to the processor, a second conductor leading from the switching element to a first end of a fuse filament in a second portion, and a third conductor leading from a second end of the fuse filament to the second spade connector.

In one embodiment the hardware component comprises a compound smart fuse having a first body with a first blade connector extending from a lower surface of the first body, the first blade connector connected to a first conductor leading from the first spade connector to a switching element operated by a processor executing coded instructions from a coupled data repository, in response to a signal received via wireless communication circuitry coupled to the processor, a second conductor leading from the switching element to a female receptacle implemented through a side of the first body, and a second body having a male connector extending from a side of the second body, the male connector adapted to mate with the female receptacle of the first body, a third conductor from the male connector to a first end of a fuse element, a fourth conductor leading from a second end of the fuse element to a second blade connector through a lower surface of the second body, the first body and the second body connected by the male connector engaged to the female receptacle forming a compound fuse adapted to plug into an automobile fuse and relay center, in a manner that the first and second body may be disconnected. And in one embodiment a second female receptacle is implemented on the side of the first body proximate where the first receptacle is implemented, and a second male connector is implemented on the side of the second body proximate where the first male connector is implemented, the second female receptacle and the second male connector not coupled to conductors, providing a more secure mating of the first and the second bodies.

DETAILED DESCRIPTION OF THE INVENTION

Figure 1:
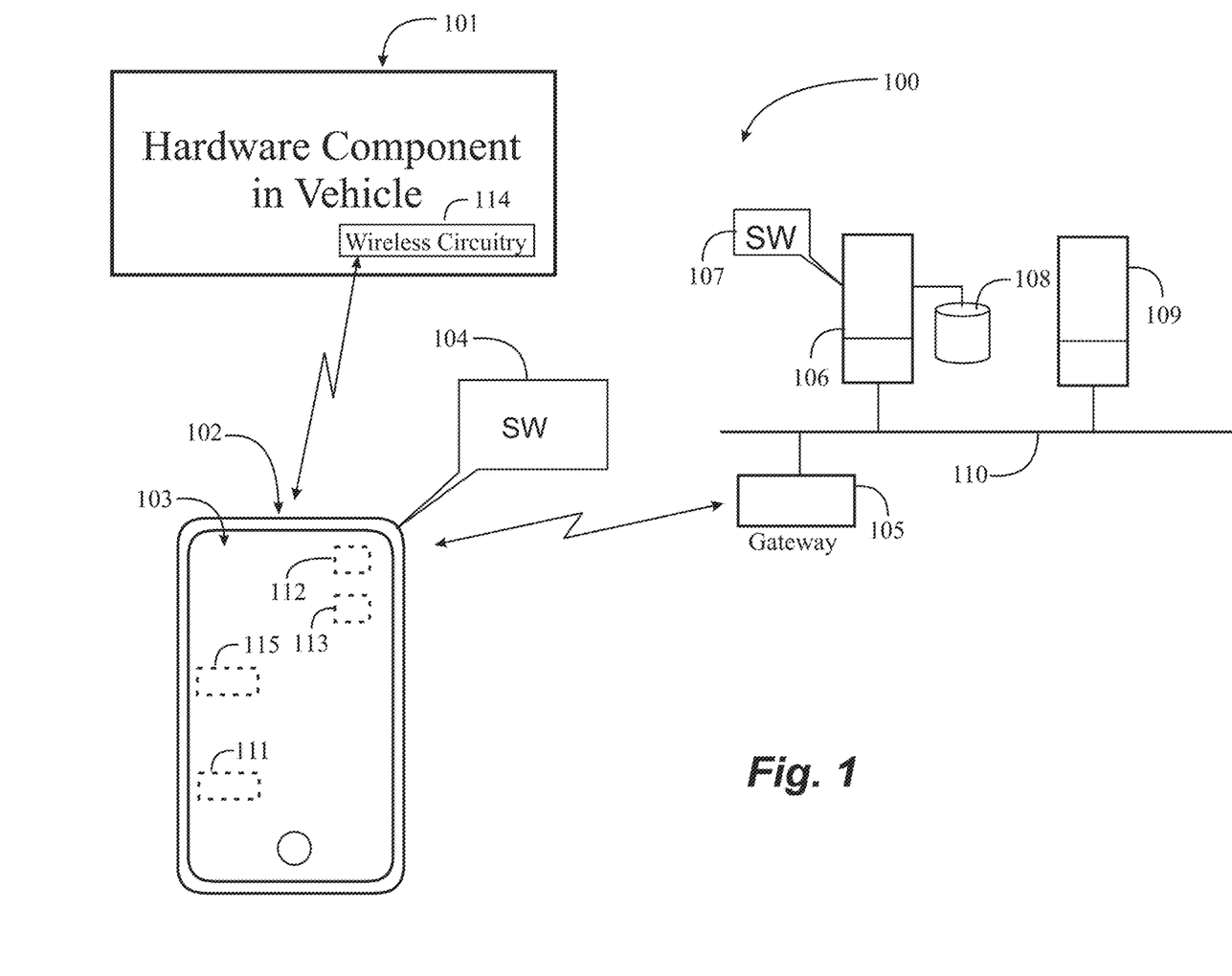
FIG. 1 is a depiction of an impairment detection and occlusion system in an embodiment of the present invention.

FIG. 1 is a depiction of an impairment detection and occlusion system 100 in an embodiment of the present invention. System 100 comprises a hardware component 101 that integrates with electronic elements of a vehicle and, under particular circumstances, prevents the vehicle from starting. Hardware component 101 may in one circumstance comprise a smart fuse replacing a fuse that provides voltage to a vehicle's starter relay, ignition, fuel pump, ECU, glow plug, or any one or more of various electrical elements and systems that must have voltage for the vehicle to start and run. In other embodiments hardware component 101 may be imposed in a line that provides voltage to any one or more of the various electrical elements and systems that must have voltage for the vehicle to start and run. The inventor believes that a smart fuse embodiment may be advantageous because it may be relatively inexpensive and simple to install.

In some embodiments of the invention hardware component 101 has wireless communication circuitry 114 adapted to communicate wirelessly with similar circuitry 115 in a portable communication device 102, which in different embodiments may be a smartphone or a pad device. Device 102 may have a display 103, that in some embodiments may be a touchscreen.

In one embodiment device 102 executes by a CPU 111 a mobile application 104. Device 102 also has a digital memory 112, as well as a microphone 113 and a speaker 111. Device 102 also in one embodiment communicates via a cellular network, or alternatively a WiFi and the well-known Internet network with a gateway 105 by which the device connects to an Internet backbone 110, representing all of the network and subnetwork connections in the Internet network. Communication may be with a server 106 executing software 107 and having a coupled data repository 108. Communication may also be made with a server 109 representing a plurality of third-party servers in the Internet network.

An IID was described above as operating as a breathalyzer interoperable with ignition circuitry to prevent a vehicle from starting. In embodiments of the invention alcohol level in breath or otherwise might not be measured. The inventive system rather relies in testing behavior that may be altered by drug, alcohol, medical or psychological impairment.

In one embodiment mobile application 104 may display one or more interactive interfaces on display 103, which may be a touchscreen display. It is well known that reaction time may be affected by different sorts of impairment. A simple test may be conducted by device 102 in which an icon or other image may be projected and the user may be expected to touch the screen in a certain way in response. The system measures the time interval in which the user responds. For example, the user may be instructed in an interactive interface that an image will be projected that is an arrow pointing in a certain direction, and the user is expected to swipe the screen in that direction as quickly as he or she may do so. The system notes the correspondence of the direction of the swipe with the arrow presented, as well as the time delay. Pass/Fail may depend on statistical archives of responses of people known to be unimpaired and people known to be impaired.

Another Pass/Fail test that may be imposed is a reading and enunciation test. The system may inform the user that a text passage will be posted, and the user is asked to recite the passage verbally. The clarity, enunciation and timing of the user's verbal response may indicate level of (or absence of) impairment. The user's response may be compared to archived results of the same test performed by persons known to be impaired or unimpaired. In some circumstances two or more Pass responses may be required for a Pass signal to be sent from device 102 to hardware component 101.

In one embodiment mobile application 104 may be provided by server 106, which may be hosted by law enforcement or by a judicial system. In court required application of system 100, as a result perhaps, of conviction for a DUI or another circumstance, performance of the person required to use the system may be recorded and archived, so the judicial or law enforcement host will have records of performance. In one embodiment the hardware component 101 may be installed by a registered and authorized service, and the user may not know where the device is installed or how it operates.

Further, in one embodiment, records of performance of specific tests may be maintained for specific persons, providing baseline data for comparison to real-time performance. For example, a person found guilty of a DUI, wherein a court may require installation of a device according to an embodiment of the present invention, may further be required to perform the tests enabled on the mobile device executing the mobile app in an embodiment of the invention, in an unimpaired state, to be recorded as a baseline for comparison to later test results, and the baseline results may be stored in a database hosted by the court, which database may be queried by the mobile app. through the Internet connection.

In some embodiments the system may employ an Accelerometer Senser—A method and system to collect and store monitoring human activity using an inertial sensor or accelerometer walking patterns for future comparisons. Also, in some embodiments the system may employ a Heat/Temperature Sensor—There may be a method and to collect an individual's temperature data over time, correlating user normal temperature data to determine the possibility of impaired abilities compared to a normal state. There may be a heart-beat Sensor/Pulse Sensor and a method to collect heartbeat signals to store for future comparisons. There may be a Proximity/GPS Sensor and a method to collect user location data over time, correlating user location data with known locations of the possibility of impaired abilities compared to a normal state. There may be a Gyroscope and a method and system to collect and store movements to determine average movements for future comparisons. There may be Eye Recognition (iris) and a method to capture normal dilation for future comparisons. There may also be an ambient light sensor.

Incorporated with server 106 or 109 there may further be a sub-system for reception, accumulation, comparison, and transmission, of data, such as:

Location Database—finds and stores geographic data where the smart device is located and matches it with different known geolocating maps. The system will force a series of tests if the location is a known location for drug or alcohol use.

Sensor Database—Stores data from the different sensor input

Voice Database—Stores an individual's voice so that it can compare the voice for future evaluations.

History Database—Stores data from different sources such as DMV, Insurance, etc., of past events.

Contributor Database—Stores a list of contributors that may have input into the evaluation criteria.

Third Party Data—storage of data from third parties that can be useful for decision-making, analysis, and comparisons.

Event Database—contains information such as the date and time of the event, the location, and other relevant details for comparison.

Approved driver database/Authorization and permissions Database—stores information about the different roles, privileges, and permissions that users have within the system.

Time Database—to store and manage time-related data, such as dates, times, time zones, and time intervals for vehicles and users.

Additional System Input Mechanisms

Input Speed—Timed measurements to tap objects on the device for future comparisons. An individual can be impaired due to the effects of alcohol or drugs on their motor coordination, reaction time, and cognitive abilities.

Speech—Times measurement of recorder words for future comparisons by capturing and processing the data recognizing speech patterns and accurately converting them into text or other types of data for comparisons.

Camera—captures images or video, to process the data and uses it as input for various applications comparisons.

Vehicle—Multiple vehicle inputs can be captured using a variety of technologies, including GPS tracking devices, telematics systems, and onboard vehicle sensors. This data can then be transmitted wirelessly to a central server, where it can be processed and analyzed including a variety of information about the vehicles, such as their location, speed, direction, fuel levels, engine performance, and more.

Sensor—devices that are designed to measure or detect various physical parameters, such as images, temperature, pressure, light, sound, or motion for future comparisons.

Biometric—unique physical or behavioral characteristics, such as fingerprints, facial features, iris patterns, or voiceprints. This data can then be used for identification, authentication, access control purposes, and future comparisons.

Third-party data generated by individuals or organizations that are not directly involved in the system or process but provide relevant information that can be useful for decision-making or analysis.

In one embodiment the system works in a flow as follows:
(a) User initiates a test to approve the operation of the vehicle.
(b) The system determines the best data to initiate a first test based on sensors or statistical data available to the system.
(c) The best test for an evaluation is started.
 If results are unclear-a second more difficult test is started.
OR
 If the results are unclear a different test is started.
Don't pass tests—the vehicle is not approved to operate.
Pass the test—the vehicle is approved to operate.

In the various operations different sensors and methods may be queried to perform the needed functions.

Other systems that may be used in different embodiments include:

Behavioral Analysis Module: Utilizes machine learning algorithms to analyze the behavior patterns of the operations of the vehicle and predict potential unauthorized use or impairment based on deviations from the norm. This could work in tandem with the Sensor and History Databases to provide a more nuanced understanding of the driver's condition.

Real-time Monitoring and Alert System: This system would actively monitor vehicle operation and driver status, sending alerts to relevant parties (such as law enforcement or emergency contacts) if it detects unauthorized use or conditions that suggest the driver is under the influence or otherwise impaired.

Feedback Loop for Continuous Improvement: Incorporating a mechanism for analyzing incidents, breaches, or false positives/negatives to refine the evaluation criteria, improve database accuracy, and update security measures. This would involve machine learning and data analytics to adjust to new patterns of behavior, emerging threats, or changes in user status.

Figure 2:
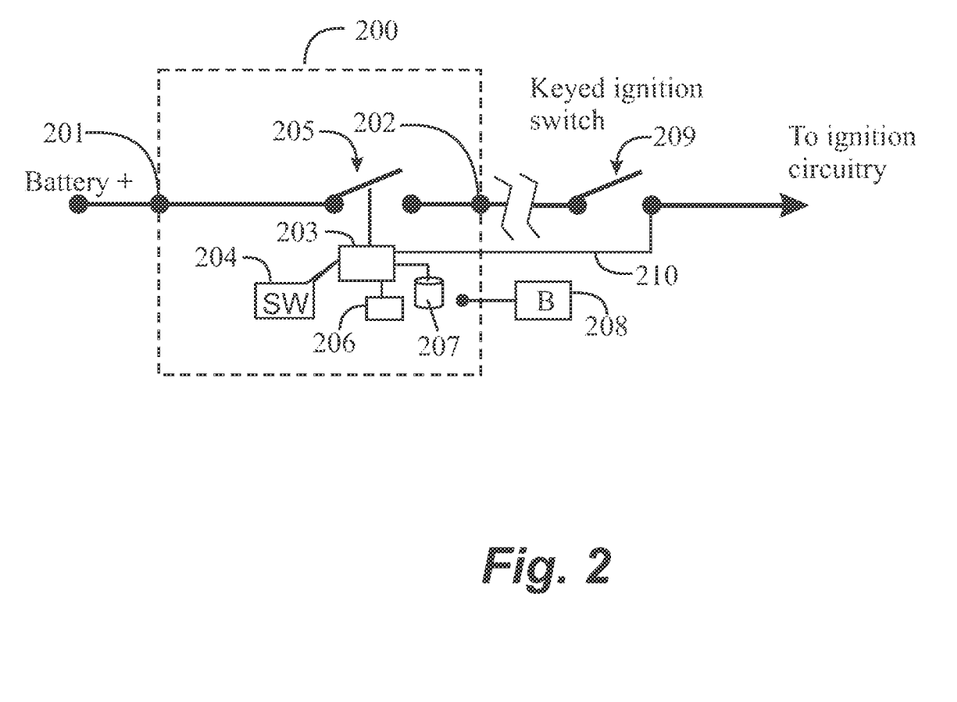
FIG. 2 is a diagram depicting a hardware component in one embodiment of the invention.

FIG. 2 is a diagram of a hardware component 200 that may be installed in an automobile such as under a dashboard or in an engine compartment on a firewall, for example. In this example component 200 may be implemented on a board or in a closed compartment with an input terminal 201 connected to battery power and an output terminal 202 connected to a keyed ignition switch of the automobile.

Hardware component 200 has a processor 203, which may be a microprocessor, executing software (SW) 204 from a data repository 207. A small replaceable storage battery 208 powers on-board electronic components. Power lines from the battery are not shown. Wireless communication circuitry 206, connected to processor 203, is enabled to receive a command wirelessly from a remote transmitter, to close a normally open contact 205. The contact closed provides voltage to output terminal 202 and hence to keyed ignition switch 209, or in some circumstances to a starter button, which, when activated provides voltage to ignition circuitry, which includes closing a starter solenoid to power the starter motor to start the automobile engine. In an alternative embodiment normally open contact 205 may be a transistor switch with necessary wiring and electrical components such as resistors.

Figure 3:
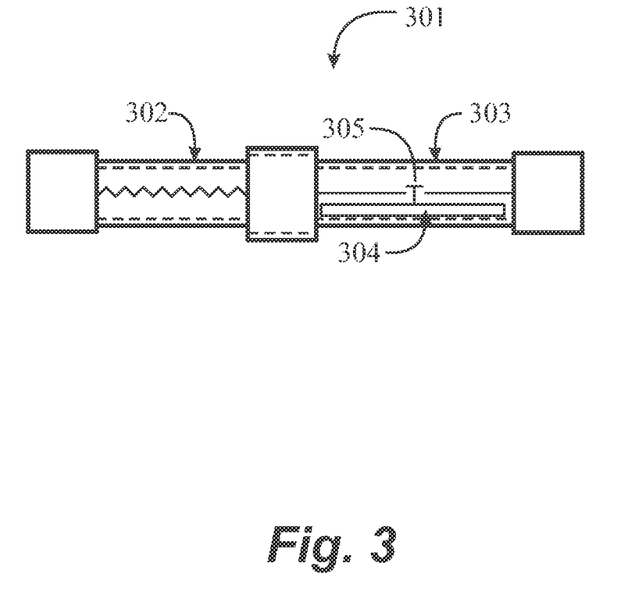
FIG. 3 is a diagram of a hardware component in another embodiment of the invention.

FIG. 3 is a diagram of hardware component 101 in one embodiment of the invention, implemented as a compound smart fuse 301. Compound smart fuse 301 replaces an original fuse that may have the length of the compound fuse and an internal element that fails or opens in event of exceeding a threshold amperage, as is common with fuses. Compound fuse 301 has a first portion 302 which is shorter than the original fuse but has a failure element that fails at the same threshold as the fuse replaced. Compound fuse 301 has a smart fuse portion 301 that has a CPU 304 and wireless communication circuitry. The CPU is adapted to open and close a contact 305 in response to a signal from device 102 (FIG. 1). The separate portions of compound fuse 301 fit together linearly, such that, in the event the fuse portion 302 is blown, it may be removed and replaced, reconnected to smart fuse portion 303.

In one embodiment of the invention a hardware component 101 is installed as a compound fuse by removing the original fuse that provides voltage to any one or a combination of several elements in the vehicle that are required for the vehicle to start and run, such as ignition, starter, fuel pump, etc.

Figure 4A:
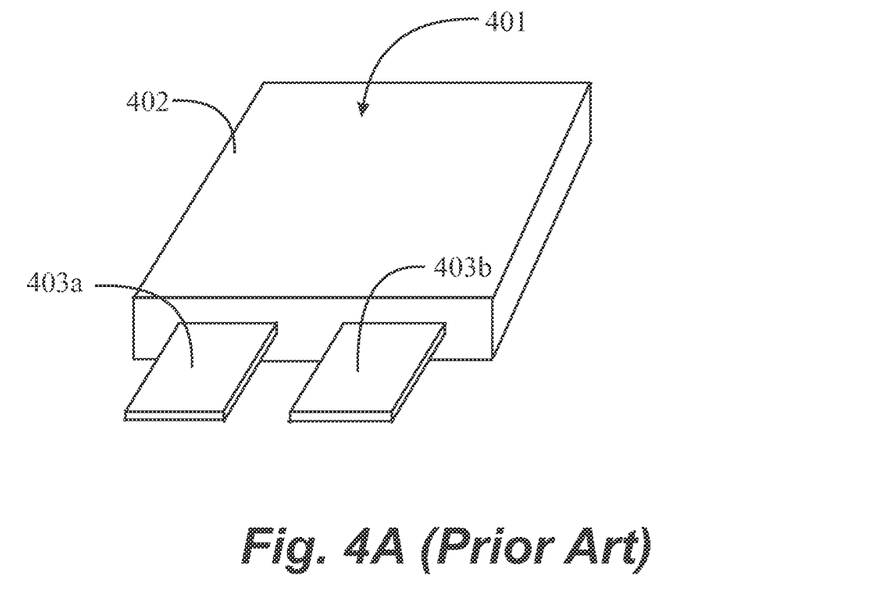
FIG. 4A is a perspective view of an automotive fuse in prior art.

In the embodiment illustrated in FIG. 3 the compound smart fuse replaces a cylindrical fuse in a fuse box typically associated with older automobiles. More modern automobiles typically have a fuse box, usually under the hood of the automobile, sometimes called a fuse and relay center, that incorporates fuses and relays that plug into an electrical board by spade connectors. FIG. 4A illustrates a conventional fuse 401 in a form factor to be used with such a more modern fuse and relay center. In the conventional fuse a body 402 has extending blade contacts 403a and 403b that are adapted to plug into sockets in the fuse and relay center.

Figure 4B:
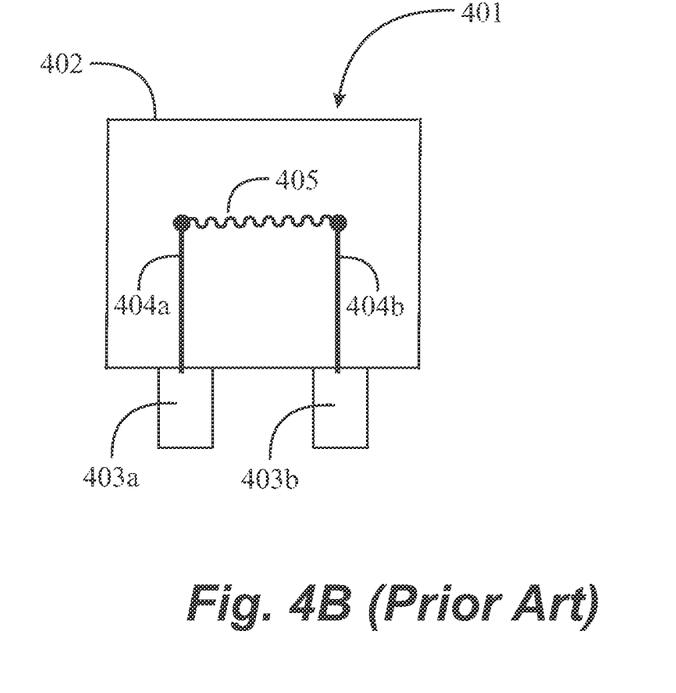
FIG. 4B is an elevation view of the prior art fuse of FIG. 4A showing internal elements.

FIG. 4B illustrates fuse 401 of FIG. 4A opened to show internal components. Conductors 404a and 404b extend from blades 403a and 403b in the fuse, and a fuse filament 405 is connected across the conductors, such that current to whatever component in the automobile is powered by fuse 401 passes through the filament. The filament is sized such that a current over a specific current will cause the filament to burn out, and the circuit will open.

Figure 4C:
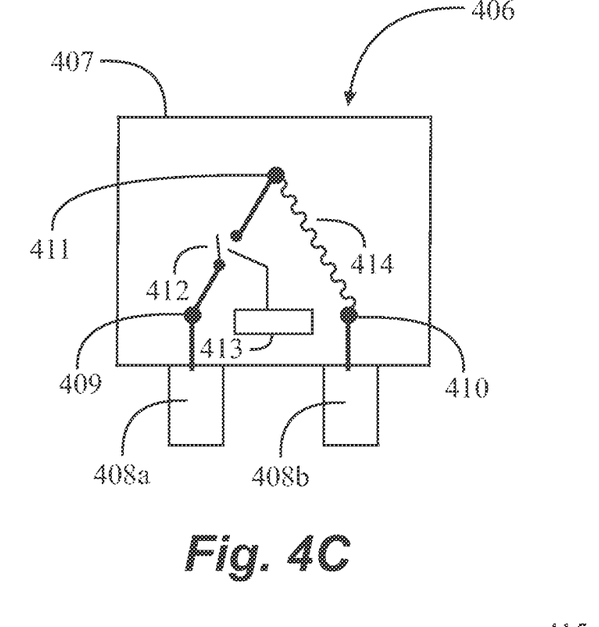
FIG. 4C is an elevation view of a smart fuse in an embodiment of the invention showing internal elements.

FIG. 4C illustrates a smart fuse 406 according to an embodiment of the invention, wherein the smart fuse powers the starter relay that in turn operates the starter solenoid. Smart fuse 406 has a body 407 with blades 408a and 408b, which are connected to internal junction points 409 and 410 respectively. A remotely operable switch 412 is imposed in a conductor between junction point 409 and a central junction point 411. Electronics 413 comprise a processor, such as a microprocessor, a data repository, coded instructions (Software) and wireless communication circuitry that are adapted to open and close switch 412 when signaled remotely from a portable communication device, such as device 102 described above. The electronics and switch 412 may be implemented as a printed circuit board with the switch comprising such as a MOSFET device. The skilled person will understand that there are a variety of ways that the necessary functions may be implemented by solid state devices.

A fuse filament 414 is implemented between central junction point 411 and junction point 410, such that in operation with switch element 412 closed the fuse filament protects the device powered by the smart fuse.

In the format depicted by FIG. 4C, when a subject interacts with one or more interactive interfaces displayed on display screen 103 of portable device 102 to qualify to start the vehicle, if the subject qualifies, the portable device sends a wireless signal to the smart fuse, which closes contact 412 for a predetermined time, such as, for example, 15 seconds. The subject turns the key switch or presses the start button, and the car will start. After the predetermined time the switch opens, but the car will continue to run. If the subject stops the car and turns off the ignition, the process must be repeated to start the automobile again.

The skilled person will understand that in the format of FIG. 4C, if the fuse filament blows, the fuse must be removed and replaced, and the electronic elements of the smart fuse are lost as well.

Figure 4D:
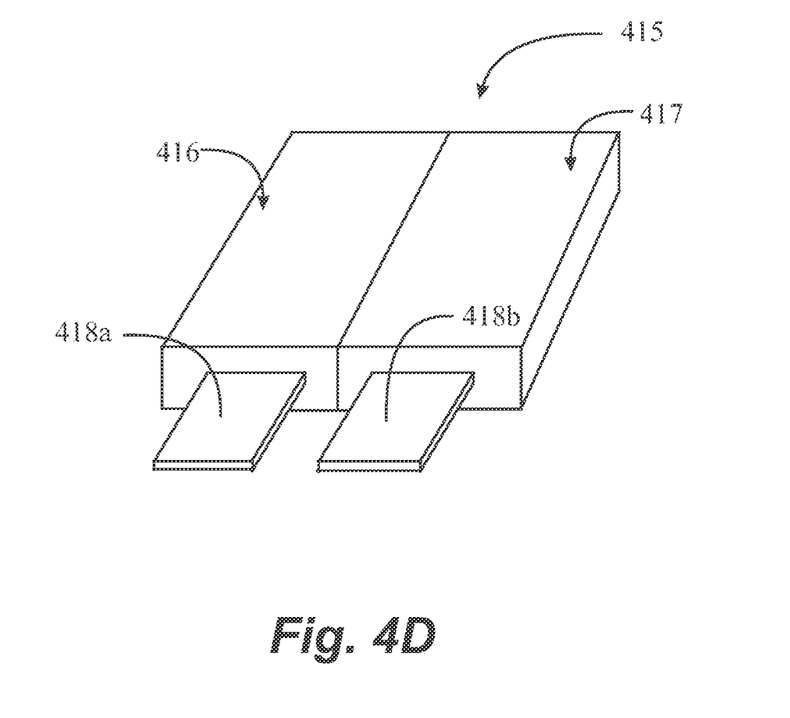
FIG. 4D is a perspective view of a two-part separable smart fuse in an embodiment of the invention.

In an alternative embodiment a smart fuse is provided wherein the smart fuse is a compound device with the functions of the fuse filament and the switching element separated. FIG. 4D illustrates a smart fuse 415 comprising a first body 416 and a second body 417. Body 416 comprises the electronics and switching elements, and body 417 comprises the fuse elements. Body 416 has a blade contact 418a and body 417 has a blade contact 418b.

Figure 4E:
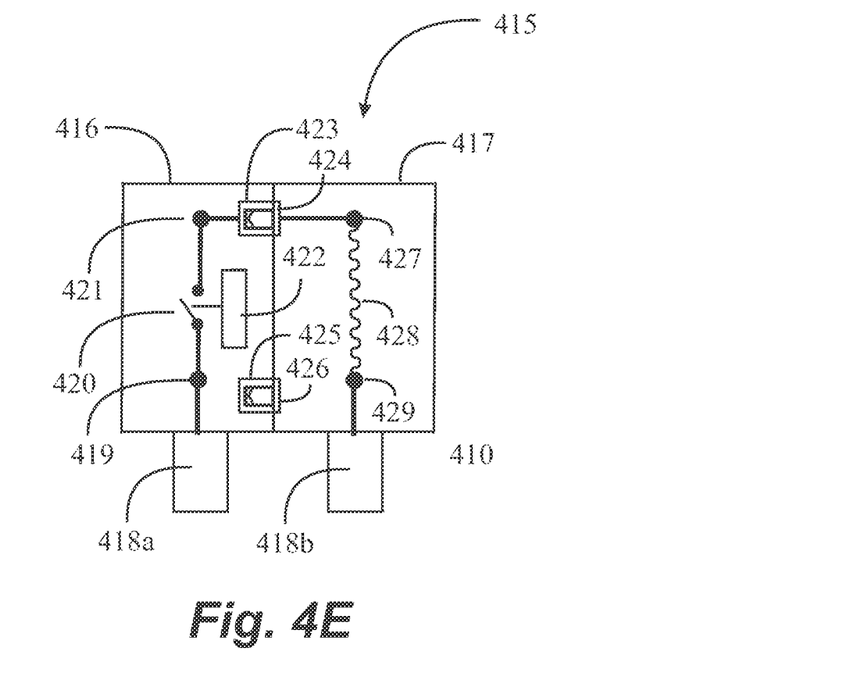
FIG. 4E is an elevation view of the smart fuse of FIG. 4D showing internal elements.

FIG. 4E illustrates separable smart fuse 415 showing internal elements. Body 416 has a junction point 419 connected by a conductor to blade contact 418a. A switch 420 is implemented in a conductor between junction point 419 and another junction point 421. The switch is controlled by electronics 422 that comprise the processor, data repository, software and wireless communication circuitry. Junction point 421 connects to a receptacle 423 which engages with a plug 424 in body 417. Plug 424 connects to a junction point 427 in body 417. A fuse filament connects between junction point 427 and another junction point 429 that connects to blade contact 418b. A second plug and socket comprising plug 426 and socket 425 is provided to ensure a secure engagement of body 416 and 417.

Figure 4F:
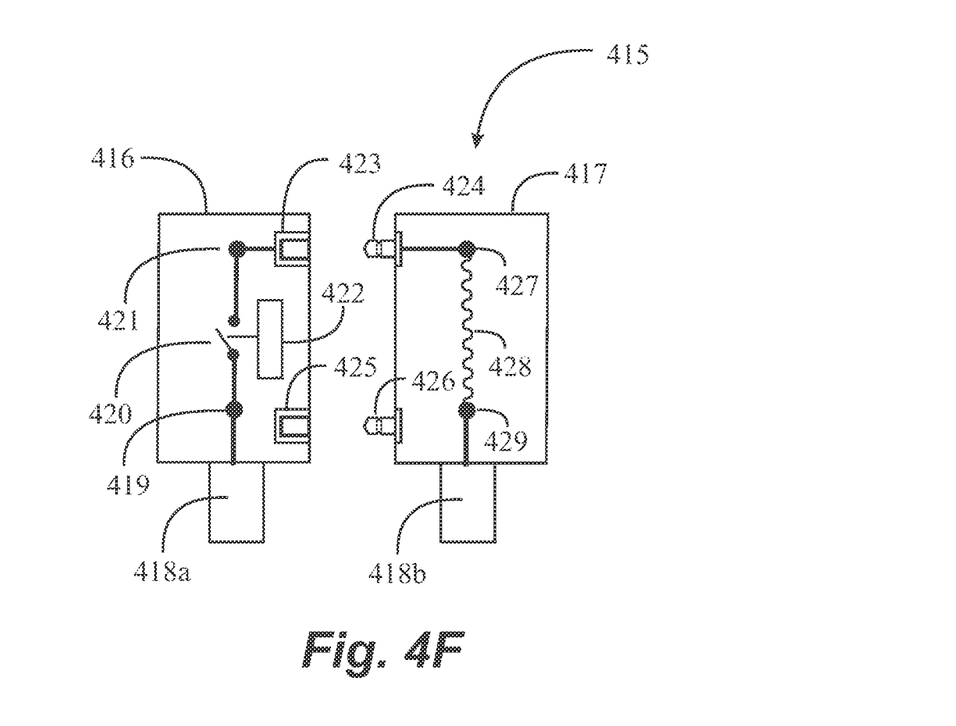
FIG. 4F is a view of the separable smart fuse of FIG. 4E with the bodies separated.

FIG. 4F illustrates body 416 disconnected from body 417. The element numbers and parts are the same as described above for FIG. 4E. When and if fuse filament 428 blows, a user may remove the compound smart fuse from its engagement in the fuse and relay center, and may separate body 416 from body 417. Body 417 may be discarded and replaced and the new body 417 plugged into body 416. This implementation saves the electronics and switching elements.

A skilled person will understand that the apparatus, methods and embodiments described are entirely exemplary and do not limit scope of the invention, which is limited only by the claims that follow.

I claim:

1. A system preventing a vehicle, from starting comprising:

a mobile application executing on a portable communication device having a display screen, user-operable input elements, a microphone audio input, a speaker and wireless communication circuitry;

a smart fuse with a body having a first and a second spade connector plugged into an automobile fuse and relay center, a first conductor leading from the first spade connector to a switching element operated by a processor executing coded instructions from a coupled data repository, in response to a signal received via wireless communication circuitry coupled to the processor, a second conductor leading from the switching element to a first end of a fuse filament in a second portion, and a third conductor leading from a second end of the fuse filament to the second spade connector; and an interactive interface displayed on the display screen;

characterized in that the interactive interface requests specific action, records a response to the request, determines if the response indicates impairment, and if not impairment, signals the smart fuse wirelessly to close the switching element for a predetermined time, enabling the vehicle to start.

2. The system of claim 1 wherein, after the predetermined time, the switching element is returned to an open status.

3. The system of claim 1 wherein the display screen is a touchscreen, and the specific action requested is a touch screen action indicated by one or more of display elements and text.

4. The system of claim 3 wherein the display screen displays an arrow, and instructions are provided by either text or audio to swipe the screen in the direction of the arrow displayed.

5. The system of claim 4 wherein reaction time is measured and compared to stored reaction times in determining impairment.

6. The system of claim 1 wherein the display screen displays a text entity, and a response is requested either by text or by audio to read the text entity aloud.

7. The system of claim 6 wherein reading of the text entity is recorded through the microphone, and compared to stored recordings by impaired and by unimpaired persons in a process of determining impairment.

* * * * *